(12) United States Patent
Miragliotta et al.

(10) Patent No.: US 6,528,318 B1
(45) Date of Patent: Mar. 4, 2003

(54) SCATTER CONTROLLED EMISSION FOR OPTICAL TAGGANTS AND CHEMICAL SENSORS

(75) Inventors: Joseph A. Miragliotta, Ellicott City, MD (US); Richard C. Benson, Highland, MD (US); Robert Osiander, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/519,320

(22) Filed: Mar. 6, 2000

(51) Int. Cl.⁷ .............................................. C09K 11/00
(52) U.S. Cl. ...................... 436/56; 252/408.1; 422/55; 422/119; 250/458.1
(58) Field of Search ............... 252/301.16, 301.4 R, 252/408.1; 283/74; 422/55, 57, 119; 436/56, 172; 250/458.1, 459.1

(56) References Cited

U.S. PATENT DOCUMENTS

| | | | | |
|---|---|---|---|---|
| 5,294,402 A | | 3/1994 | Schrepp et al. ................ 422/57 |
| 5,498,549 A | * | 3/1996 | Nagel et al. .................. 422/55 |
| 5,643,728 A | | 7/1997 | Slater et al. .................... 435/6 |
| 5,763,891 A | * | 6/1998 | Yoshinaga et al. ........... 250/271 |
| 5,843,650 A | | 12/1998 | Segev ............................. 435/6 |
| 5,900,215 A | * | 5/1999 | Seifert et al. .................. 356/39 |
| 5,912,257 A | | 6/1999 | Prasad et al. ................ 514/356 |
| 5,932,309 A | | 8/1999 | Smith et al. ................... 428/46 |
| 5,935,755 A | | 8/1999 | Kazmaier et al. ........... 430/120 |
| 5,953,112 A | | 9/1999 | Rosow et al. .............. 356/73.1 |
| 5,974,150 A | * | 10/1999 | Kaish et al. .................... 283/85 |
| 6,040,194 A | * | 3/2000 | Chick et al. ............. 422/82.07 |
| 6,214,563 B1 | * | 4/2001 | Negulescu et al. ...... 422/82.05 |
| 6,297,059 B1 | * | 10/2001 | Song et al. ............... 435/287.1 |
| 6,402,986 B1 | * | 6/2002 | Jones et al. .............. 250/459.1 |
| 6,410,255 B1 | * | 6/2002 | Pollok et al. .................. 435/21 |

* cited by examiner

Primary Examiner—Jeffrey Snay
(74) Attorney, Agent, or Firm—Francis A. Cooch

(57) ABSTRACT

Sensors and/or taggants feature high optical gain materials which are disposed in a high scattering environment. These materials, when adequately excited, emit intense and spectrally narrow light that is dependent on the chemical environment in which high gain materials are dispersed. When two materials are placed in the same high scattering environment, the spectal emission properties of each emitter will depend on the chemical composition of the surrounding medium. The switching or transferring of energy from one emitter to the other when the chemical environment is changed in a specific manner is enabled and a shift in the spectral emissions can be detected and/or predicted.

18 Claims, 12 Drawing Sheets

SCATTER CONTROLLED EMISSION FOR OPTICAL TAGGANTS AND CHEMICAL SENSORS

BACKGROUND OF THE INVENTION

1. Field of the Invention

The present invention relates generally to an arrangement which exploits scatter-controlled emissions for chemical sensor or taggant arrangements and more specifically to an arrangement which permits an increase in the security of scatter-controlled emissions, and/or which permits a small change in a chemical environment to be detected.

2. Description of the Related Art

Various attempts have been made to develop taggant arrangements. One example of this can be found in U.S. Pat. No. 5,763,891 issued to Yoshinaga, et al. on Jun. 9, 1998. This arrangement is such that an identification mark is formed using a plurality of recording materials having fluorescent characteristics in wavelength regions that almost overlap each other but which are such that the maximum absorbing characteristics of each occurs at different wavelengths. Thus, in order to detect the presence of the unique combination of fluorescing material, it is necessary to sequentially irradiate a target containing these materials with two different light sources, or at least a source, which is capable of sequentially emitting radiation at two different distinct frequencies.

A further problem which is encountered with this arrangement is that the two fluorescing agents that are contained in an ink or the like type of carrier, are arranged to be sensitive to radiation in a near infrared region, and to have absorption spectrums wherein the maximum wavelengths do not overlap each other. This greatly inhibits the use of such materials outdoors or in environments wherein, merely by way of example, heat from hot machinery or objects lying in the hot sun, and/or the sun itself, are apt to produce so much background IR noise as to render such a taggant useful only in special controlled environments.

On the other hand, an example of a sensing arrangement, which utilizes fluorescing materials, is found in U.S. Pat. No. 5,498,549 issued to Nagel et al. on Mar. 12, 1996. This arrangement is direct to sensing the concentration, for example, partial pressure, of a component or analyte of interest, such as oxygen, in a medium, for example, an aqueous-based medium, such as blood. The aim of this arrangement is to provide accurate, reliable and reproducible concentration determinations, and to enable such determinations in spite of signal transmission problems, such as, bent optical fibers, and other operational difficulties which may affect the quality of the signals being transmitted.

Nevertheless, these arrangements are individually limited in their scope of application and the underlying technology cannot be applied to both sensor and taggant arrangements.

SUMMARY OF THE INVENTION

The invention centers on the novel emissive properties of high optical gain materials in a high scattering environment. High optical gain materials emit intense and spectrally narrow light that is dependent on the chemical environment in which high gain materials are contained. When two high-gain materials are placed in the same environment, the properties of each emitter will depend on the chemical composition of the surrounding medium. The invention enables the switching or transferring of energy from one emitter to the other when the chemical environment is changed in a specific manner. Thus, a shift in the spectral emissions can be detected, caused and/or predicted.

While this concept can be applied to a wide variety of different technologies, identifying taggants and sensors are two exemplary forms of application. In the case of a taggant, various possibilities are presented. Merely by way of example, it is possible to impregnate a polymer with at least two optically high gain materials which, for the sake of explanation, shall be referred to as emitters, and to form a thread, fiber, particle, film surface or the like with the thus modified polymer. By engineering the polymer to be selectively porous to one or both liquids or gases (or both), it is possible to place an article in a testing device and to irradiate it to the degree that one of the emitters will be excited to a stimulated level and emit photonic energy at a first expected wavelength. By applying a spray (merely by way of example) containing a predetermined analyte or mediating material, the wavelength will, in the case of a genuinely tagged fiber, shift to a second known wavelength. If this shift is ascertained, then the article being examined can be deemed to have been positively identified.

In the same manner a gas "sniffer" type sensor (for example) can be created in a manner wherein, if the shift from one wavelength to the other is detected, then the presence of a predetermined gas can be ascertained, and a warning, if it is necessary, issued. It should, of course, be appreciated that many and varied variants are possible without deviating from the concept upon which the present invention is based.

More specifically, scatter controlled emission is an optical scattering process that produces stimulated emission from random media with high-gain. The high-gain media for scatter controlled emissions in an embodiment of the invention resides in a mixture of laser dye molecules and submicron scatters dispersed in either a liquid or a solid host material. The emission characteristics of this media fall into two categories, weak broadband features under low intensity illumination (which produces spontaneous emission) and intense, narrow band laser-like emission which occurs when the optical excitation source is above a threshold intensity level (which produces stimulated emissions).

In accordance with the present invention, the stimulated emissions from the random media have a markedly higher chemical sensitivity as compared to spontaneous emissions. By way of example, stimulated emission from a methanol solution containing two laser dyes (4-dicyanmethyline-2-methyl-6-(p-dimethylaminostyryl)-4H-pyran (DCM) and Carbazine 720), in the presence of $10^{10}/cm^3$ concentration of titanium dioxide particles (sizes ranging from a few micrometers to less than one micrometer), was able to detect parts per million benzylamine (relative to the dye concentration) in the scattering medium.

Another advantage of this invention is the ability to generate small and efficient light sources, which can serve as replacements for more complex and expensive conventional laser systems. This is due to the composition of the random media, which contain both the active laser material and the feedback mechanism (scatterers). A suitable pump source for excitation is however, required.

A first aspect of the invention resides in a photonically excitable arrangement comprising: a first material which is capable of absorbing and emitting photonic energy and which, when sufficiently excited by photonic energy from an external source, emits stimulated radiation in a first narrow wavelength band; a second material which is capable of absorbing and emitting photonic energy; and a mediating material which causes the photonic emission of the first material to be transferred to the second material which is excited to emit stimulated radiation in a second narrow wavelength band at least partially in place of the emission from the first material in the first narrow wavelength band. This arrangement further comprises a host material in which the first and second materials are dispersed, and scattering particles dispersed amongst the first and second materials for scattering emissions from the first material to the second material.

In this arrangement the mediating material is selected to modify the first material and to change at least one of its characteristics to the degree that the photonic radiation which is emitted from the first material under stimulated conditions, is changed to a form wherein it is absorbed by the second material. A laser can be used as the source.

The scattering particles can be selected from, but not limited to, the group consisting essentially of: silicon carbide, diamond, alumina, barium titanate, zinc oxide and titanium dioxide. The first material is selected from, but not limited to, the group consisting essentially of rhodamine green, DCM, coumarin dyes, fluorescein, anthracene dicarboxaldahyde, and napththalene dicarboxaldahyde. On the other hand, the second material is selected from, but not limited to the group consisting essentially of: seminaphthorhodfluor dyes, dimers of cyanine dyes, hydroxypyrene trisulfonic acid, magnesium orange, BODIPY, fluorescein, and carbazine.

In some embodiments the host can be a polymer structure formed to have a predetermined permeability to fluid material into which a mediating material selected from, but not limited to, the group consisting essentially of: nucleic acid, carbon dioxide, a metal ion, aromatic amine, cyanide, and thiol, can introduced.

A second aspect of the invention resides in a sensor arrangement comprising: a source of photonic energy which emits photonic energy of a photonic level sufficient to induce stimulated emissions from irradiated materials; a cell into which the photonic energy from said source is directed, the cell including a host material in which first and second photonically responsive materials, and scattering particles are dispersed, said first photonically responsive material being excited by exposure to photonic energy from said source to emit stimulated photonic energy in a first frequency range, said cell being adapted to have a mediating material introduced thereinto which causes the photonic energy in the first frequency range, to be transmitted to and absorbed by the second photonically responsive material which becomes sufficiently excited to emit photonic energy in a second frequency range; and a photonically responsive device responsive to the stimulated photonic emissions from the cell for determining the frequency or frequency range of the photonic emissions emitted by the cell during excitement by the source of photonic energy.

As in the previous aspect, the source of photonic energy comprises one of a continuous wave and a pulsed laser, while the first material is selected from the group consisting essentially of: rhodamine green, DCM, coumarin dyes, fluorescein, anthracene dicarboxaldahyde, napththalene dicarboxaldahyde; and the second material is selected from the group consisting essentially of: seminaphthorhodfluor dyes, dimers of cyanine dyes, hydroxypyrene trisulfonic, magnesium orange, BODIPY, fluorescein, and carbazine. The photonically responsive device comprises a photometer or a CCD camera.

A third aspect of the invention resides in a sensing method comprising: using a source of photonic energy to irradiate a mixture of first and second photonic excitable materials; sensing a frequency or frequency range of photonic emissions from the mixture; introducing a mediating material into the mixture; and detecting a change in the frequency or frequency range on photonic emissions which occurs due to a presence of the mediating material. In addition to these steps it is within the scope of this aspect to include the steps of: sensing the intensity of photonic emissions from the mixture in the absence of the mediating material; and sensing the intensity of photonic emissions from the mixture in the presence of the mediating material.

This method may further include the steps of: monitoring a decrease in photonic emissions in a first frequency range and a corresponding increase in photonic emissions in a second frequency range which occurs in response to a change in an amount of mediating material introduced into the mixture.

A further aspect of the invention resides in a method of taggant examination comprising the steps of: preparing a mixture of first and second photonically responsive materials, scattering particles and a mediating material, the first and second photonically responsive materials being excited by exposure to photonic energy to respectively emit photonic energy in first and second frequency ranges; incorporating the mixture into a carrier; disposing the carrier with a surface which is to be identified; irradiating the surface with a beam selected to excite the first material to emit stimulated emissions; detecting the frequency at which the stimulated emission occurs; introducing a mediating analyte into the mixture; and detecting a change in frequency which occurs as a result of the introduction of the mediating analyte. This method may further comprise the steps of: sensing the intensity of the stimulated emission at a first frequency prior to introduction of the mediating analyte; sensing the change in intensity with a change in mediating analyte; and sensing the increase of the intensity of the emission at a second frequency as the concentration of the analyte increases.

Another aspect of the invention resides in a taggant comprising: a fluid permeable host material exposable to beam of photonic energy from a source which is remotely located from the host material; first and second photonically responsive materials which are dispersed through the host material; and reflecting particles which are dispersed in the host material with the first and second photonically responsive materials to establish a high optical gain media through which photonic energy can be amplified and reflected back to a remote detector. In this arrangement also, the scattering particles are selected from, but not limited to the group consisting essentially of: silicon carbide, diamond, alumina, and barium titanate, zinc oxide and titanium dioxide.

The host material in this instance can be formed of a fluid permeable polymeric structure.

BRIEF DESCRIPTION OF THE DRAWINGS

The various features and advantages of the present invention will become more clearly appreciated from the following description of the preferred embodiments of the invention when taken with the appended drawings in which:

FIGS. 9–13 are graphs which depict in terms of emission intensity and wavelength, various relationships/characteristics which demonstrate the effect produced by an example of the present invention, and wherein:

FIG. 9 shows emission from a Pyrromethane 567 dye solution with (♦) 0,(O) $2.3\times10^{10}$, (□) $4.6\times10^{10}$, (x) $9.2\times10^{10}$, and (•) $18.4\times10^{10}$ $TiO_2$ particles/$cm^3$.

FIG. 10 shows spontaneous emission from a Rhodamine 610 solution with a $4.6\times10^{10}$ $cm^3$ $TiO_2$ particle concentration. The spectra were recorded (•) with and (o) without 1.2 $\mu$g KOH in the solution.

FIG. 11 shows stimulated emission from a Rhodamine 610 solution with a $4.6\times10^{10}$ $cm^3$. $TiO_2$ particle concentration. The spectra were recorded (•) with and (o) without 1.2 $\mu$g KOH in the solution.

FIG. 12 shows spontaneous emission from a DCM/Carbazine dye solution with a $TiO_2$ particle concentration of $1.2\times10^{11}/cm^3$. The benzylamine additions to the solution are (O) 0, (□) 200, (x) 1000, (•) and 4000 picograms.

FIG. 13 shows stimulated emission from a DCM/Carbazine dye solution with a $TiO_2$ particle concentration of $1.2\times10^{11}/cm^3$. The benzylamine additions to the solution are (O) 0, (□) 200, (x) 1000, (•) and 2000 picograms.

DETAILED DESCRIPTION OF THE PREFERRED EMBODIMENTS

Figure 1:
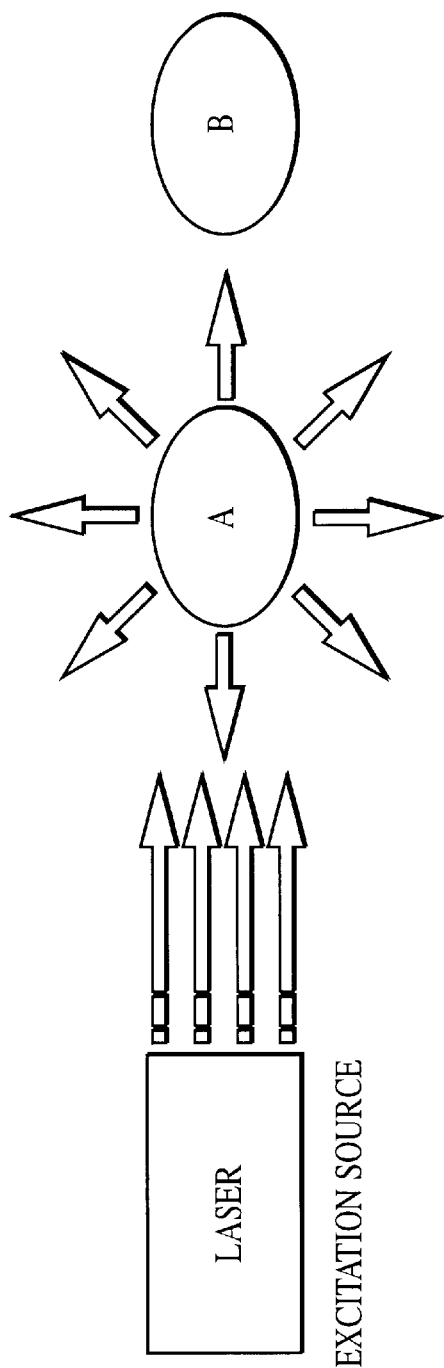
FIGS. 1 and 2 are schematic diagrams showing the situation wherein two emitters "A" and "B" are irradiated with a laser or the like type of excitation source, and one of the emitters (viz., emitter "A") absorbs the irradiated energy and becomes excited to the level of producing stimulated narrow band photonic emissions in a first narrow emission wavelength band.
Figure 2:
Figure 3:
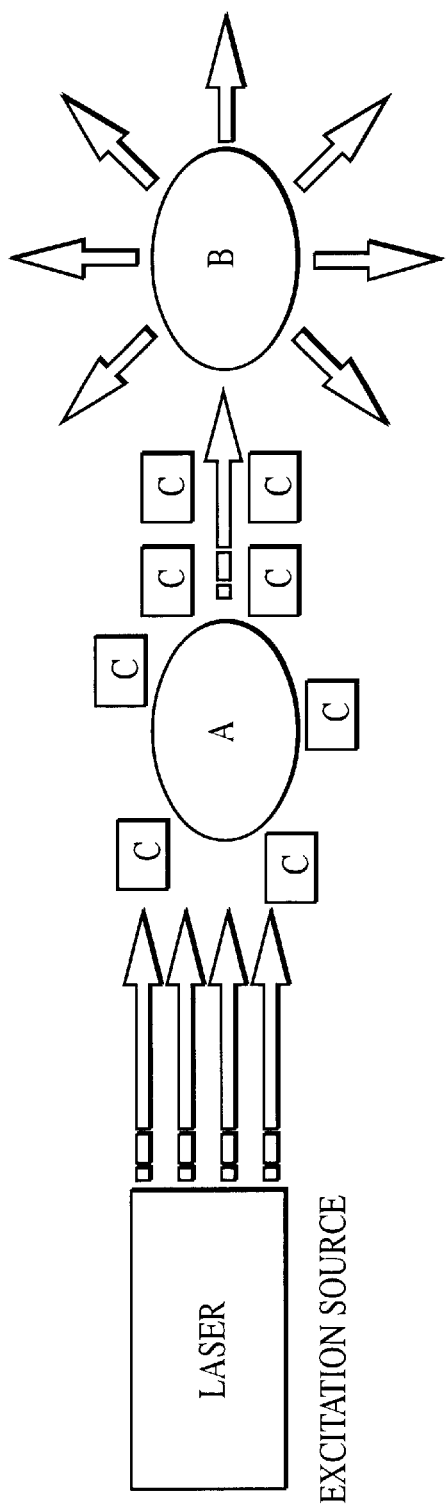
FIGS. 3 and 4 contrast the situation shown in FIGS. 1 and 2, and depict the situation wherein a mediator or analyte material "C" has been introduced into the environment and interacts with either the emitter "A" or "B". The emissions which are stimulated from emitter "A" can be efficiently coupled, i.e. energy transferred, to emitter "B" which is then stimulated to emit photonic energy in a second narrow wavelength band. The energy transfer process induces a shift in the emissive properties of the "A" and "B" mixture of emitters.

As illustrated in FIGS. 1–6, the inventive concept resides in the ability to 1) generate intense, narrow band emissions from highly scattered gain media; and 2) control the energy transfer between two emitting agents via the addition of a chemical analyte or mediating material. The addition of this material produces a small, but readily detectable shift in the emission wavelength. More specifically, as shown in FIG. 1, a shift is observable when first and second emitters "A" and "B" such as fluorescent dyes, are exposed to a source of photonic excitement. In this instance, the wavelength of the exciting photonic energy is selected to correspond to that which is absorbed by the first emitter "A". The second emitter "B" therefore remains unexcited while the first is induced to a level of excitement wherein "stimulated" emissions occur. The level of excitement, which is necessary to raise the first and second emitters "A" and "B" to the levels required in connection with the present invention, is greater than previously mentioned spontaneous emissions. The narrow frequency band in which the photonic energy is emitted by the excited emitter particles under these conditions is depicted in FIG. 2.

Figure 4:
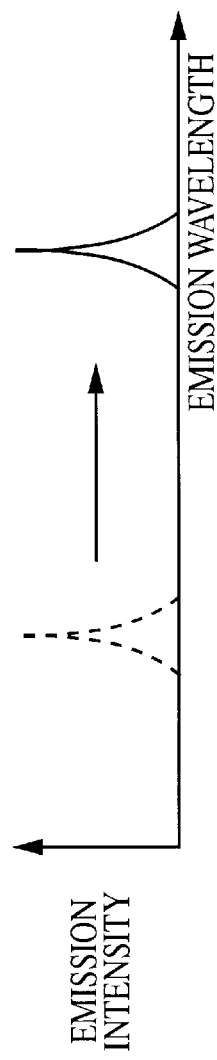
Figure 5:
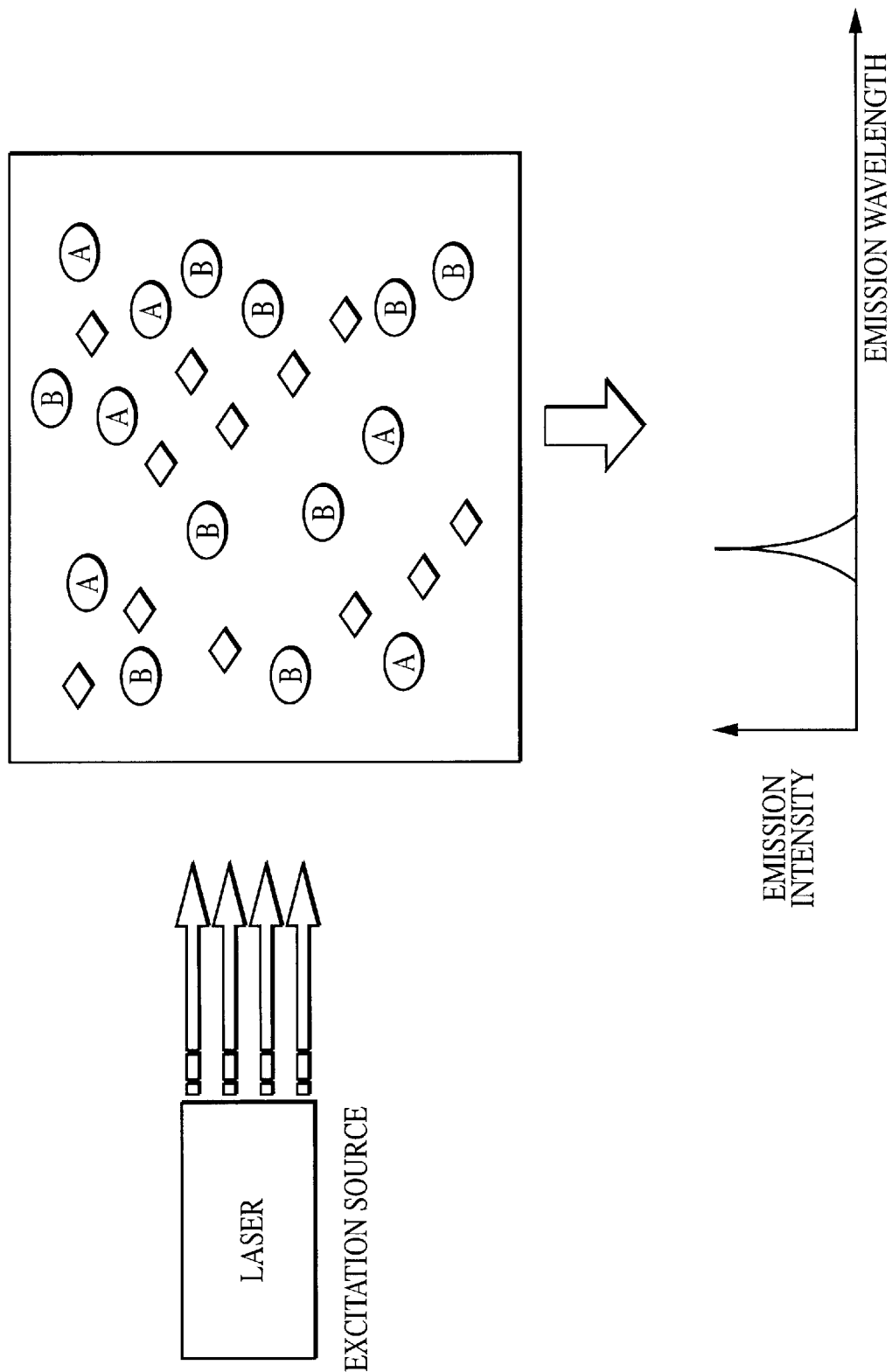
FIG. 5 schematically depicts a cell which contains a mixture of emitters "A" and "B" which are dispersed with small reflecting particles that reflect the beams of light which enter and/or are generated within the cell and amplify the cell emission.
Figure 6:
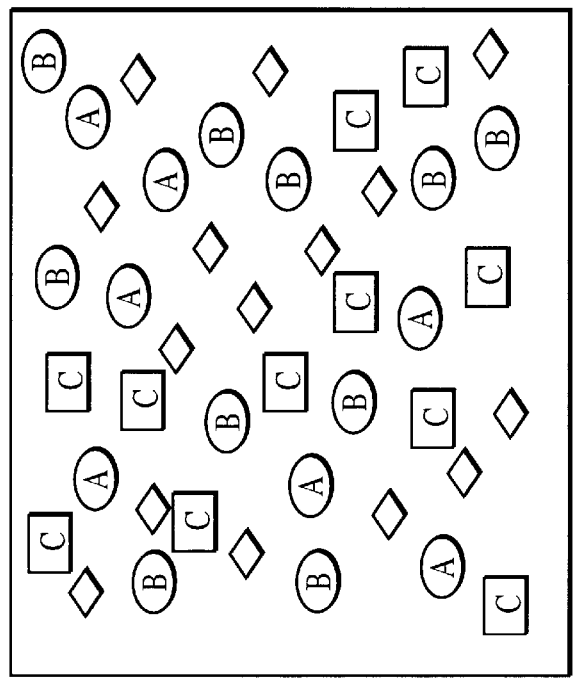
FIG. 6 is a schematic depiction of the cell shown in FIG. 5, showing the shift in the output frequency which occurs when a mediating analyte is introduced to the cell and causes photonic energy to be transferred from the "A" emitter to the "B" emitter.
Figure 6:
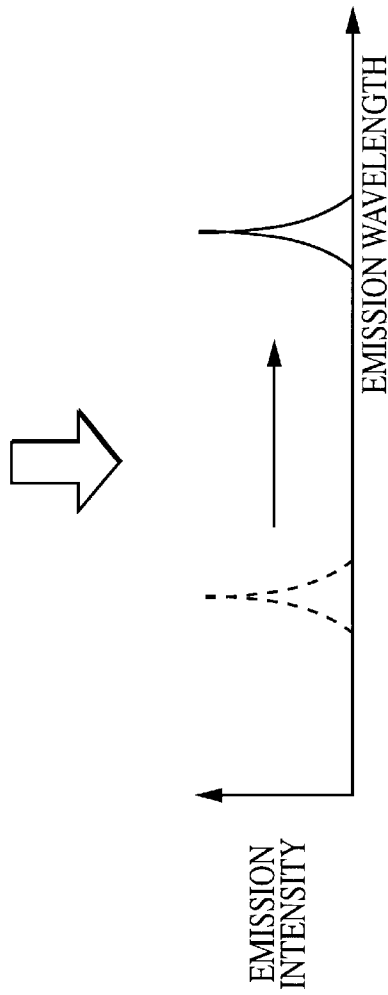
Figure 6:
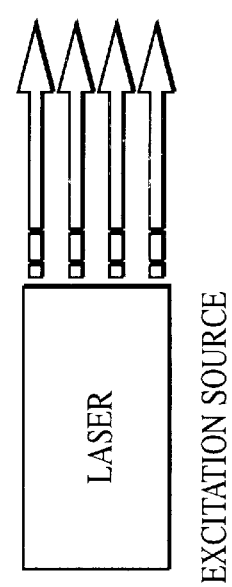

However, upon a mediating agent or analyte "C" being introduced into the environment in which the first and second emitters are disposed, a change in the emission characteristics of either emitter "A" or "B" occurs, which permits the efficient transfer of energy from emitter "A" to emitter "B. The situation as depicted in FIGS. 4 and 6 now occurs wherein a shift in spectral emissions is observed. Thus, we have a change wherein the emission regime is dominated by emitter "A" in the absence of the analyte "C" and then switched to a situation wherein the emitter "B" replaces "A" in the presence of the mediating material "C".

It is should be noted that the width of the stimulated emission peaks which are produced in accordance with the invention are typically about 5 nm in width as compared with spontaneous emissions which have a much lower intensity and a band width of about 36 nm.

In accordance with the present invention, once the addition of the analyte "C" has been made, emitter "A" is capable of efficiently transferring energy to emitter "B". In fact, as will be demonstrated later in connection with FIG. 13, as the concentration of the analyte "C" increases, the intensity of the emission from emitter "" decreases, while that of emitter "B" increases. Upon the concentration of the analyte "C" reaching a given level, the emissions from emitter "A" are seen to be extinguishing while those from emitter "B" tend to maximize since nearly all of the energy which is being released by emitter "A" is being transmitted to emitter "B".

It is important to note that the sensitivity of this arrangement is very high. This is due to the low concentrations of emitters "A" and "B" which render it possible to achieve the above-mentioned spectral shift in response to very small concentrations of analyte. By way of example, pico to femto mole analyte concentrations will enable the spectral shift to occur.

Another aspect of this arrangement resides in the ability to determine the concentration of the analyte. Given that the number of emitter "A" molecules is known, then the concentration at which the emission of emitter "A" undergoes a predetermined reduction, will have a predetermined relationship with the amount of analyte present. Thus, the manner in which the emission of emitter "A" decreases taken with the manner in which the emissions of emitter "B" increase, can be used to provide an indication of the concentration of the analyte vis-a-vis the concentrations of the two emitters.

In more detail, stimulated emission from the highly scattering, random medium is characterized by strong spectral narrowing with a corresponding enhancement to the emission intensity. The amplification process is initiated with the absorption of an incident photon (excitation source) and the subsequent emission of a photon by a dye molecule in the scattering media. The presence of a suitable concentration of scattering particles such as $TiO_2$ particles, assures that the emitted photon will be multiply scattered and confined within a small volume of the media, which is typically on the order of 100 $\mu m^3$.

The scattering process extends the path length of the emitted light within the high gain region, leading to optical amplification by stimulated emission. When the optical gain achieved by the increased scattering path length exceeds the loss mechanisms in the random media (diffuse scattering and absorption), the onset of amplification occurs. At this threshold level, the emission profile from the random media exhibits a dramatic narrowing of the bandwidth, and a corresponding linear dependence on the excitation intensity. The conditions for efficient amplification in a random media therefore depend on the optimization of gain parameters such as the absorption/emission characteristics of the emitting dye, the mean free scattering distance, and the absorptive properties of the host material.

Figure 7:
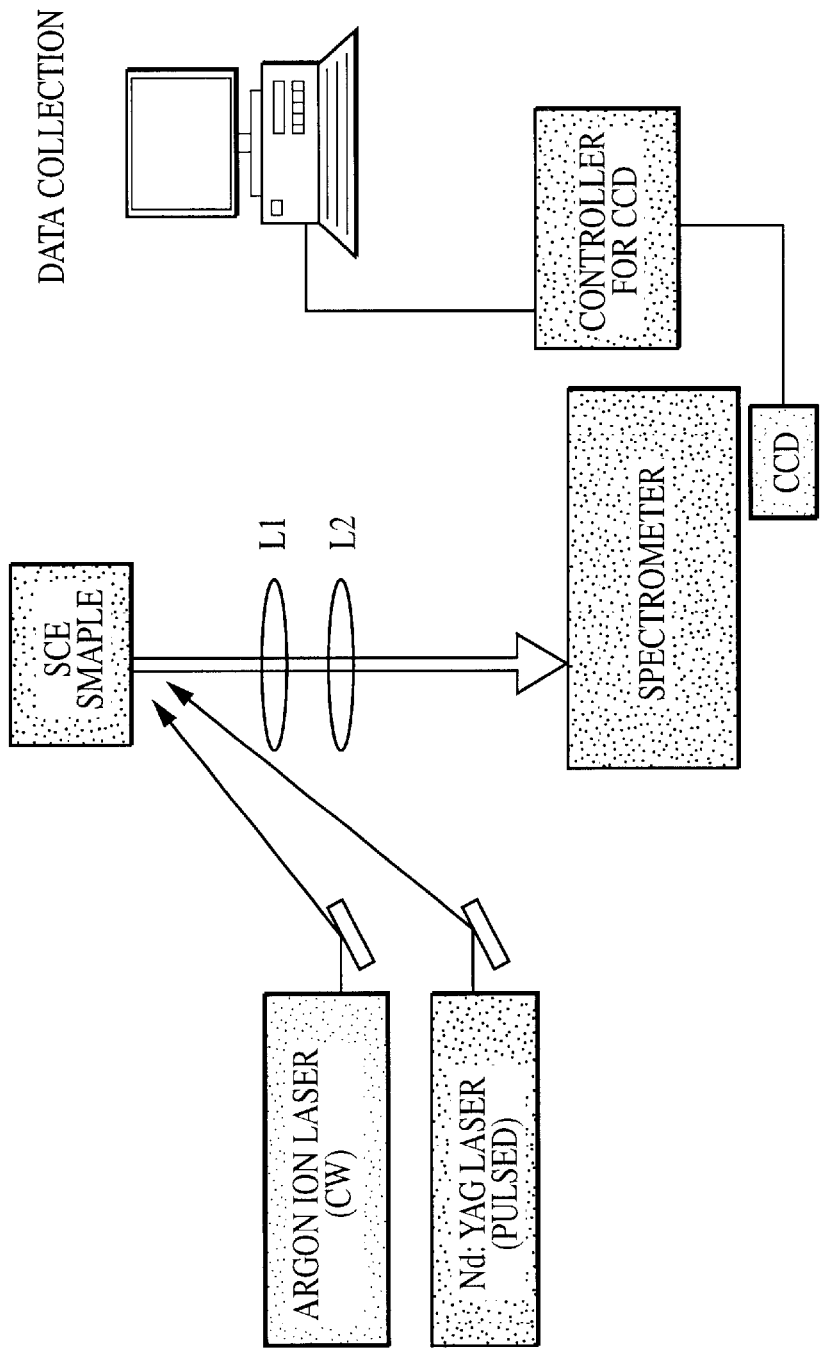
FIG. 7 is a schematic diagram showing an arrangement used to irradiate a sample and to determine the change in emission characteristics occur in response to a test mediating analyte.

FIG. 7 shows an experimental apparatus for scatterer controlled measurements. In this figure, SCE denotes a random media solution, while LI and L2 denote the collection lens for the spectrometer. As shown, the emission from the laser dye/particle solutions was generated with either a continuous wave (cw) or a pulsed laser, using by way of example, an argon ion laser (514.5 nm) or a pulsed, frequency doubled Nd:YAG laser (532 nm, 7 nanosecond pulse).

In the experiments conducted with this apparatus, the cw laser source was operated at 10 mWatt and found suitable for the generation of spontaneous emission in all dye solution samples. On the other hand, the pulsed laser was operated with pulse energy of 3 mJoule, and was also sufficient in producing stimulated emission in the amplifying media.

Optical measurements using the above mentioned lasers were carried out by focussing the incident laser beam on a 2 mm spot of a solution sample which was contained in a suitable cell and by directing the optical emissions to either a spectrophotometer or a CCD camera. Examples of these devices are a SPEX Triplemate spectrometer and a Princeton Instruments CCD camera, respectively. The data from the camera were transferred to a computer via a GPIB connection to the CCD controller.

Figure 8:
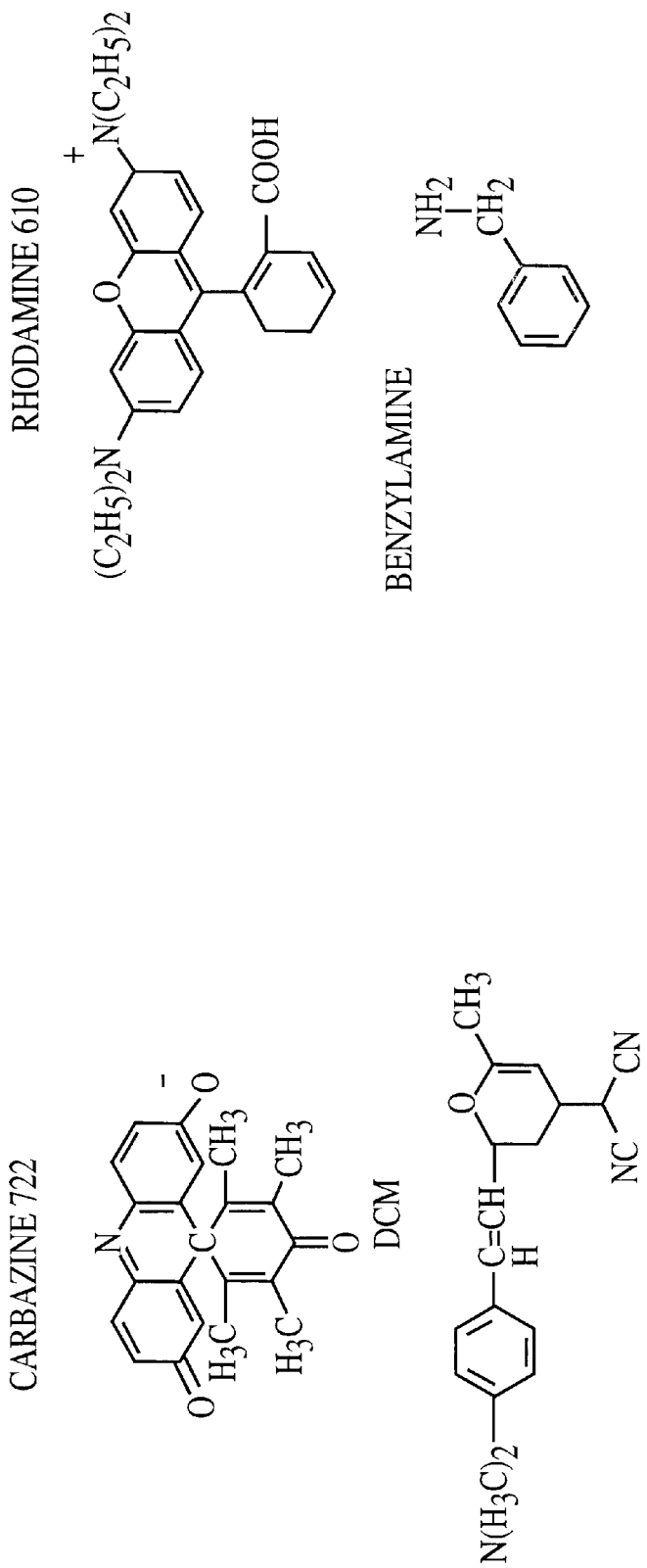
FIG. 8 are diagrams showing the chemical structure of various dyes and an aromatic amine which are used in later disclosed examples of the invention.

The laser dyes (emitters) used in the emission measurements were obtained from Exciton, Inc. (DCM, Carbazine 720, and Rhodamine 610) and Lamba Physik, Inc. (Pyrromethene 567). The $TiO_2$ particles (Ti-Pure R-900, 250 nm diameter) were obtained from E. I. Dupont de Nemours and Company. The analytes under investigation (potassium hydroxide (KOH) and benzylamine) were obtained from the Aldrich Chemical Co. and were used without purification/modification. The molecular structures of the laser dyes and benzylamine are shown in FIG. 8.

Figure 9:
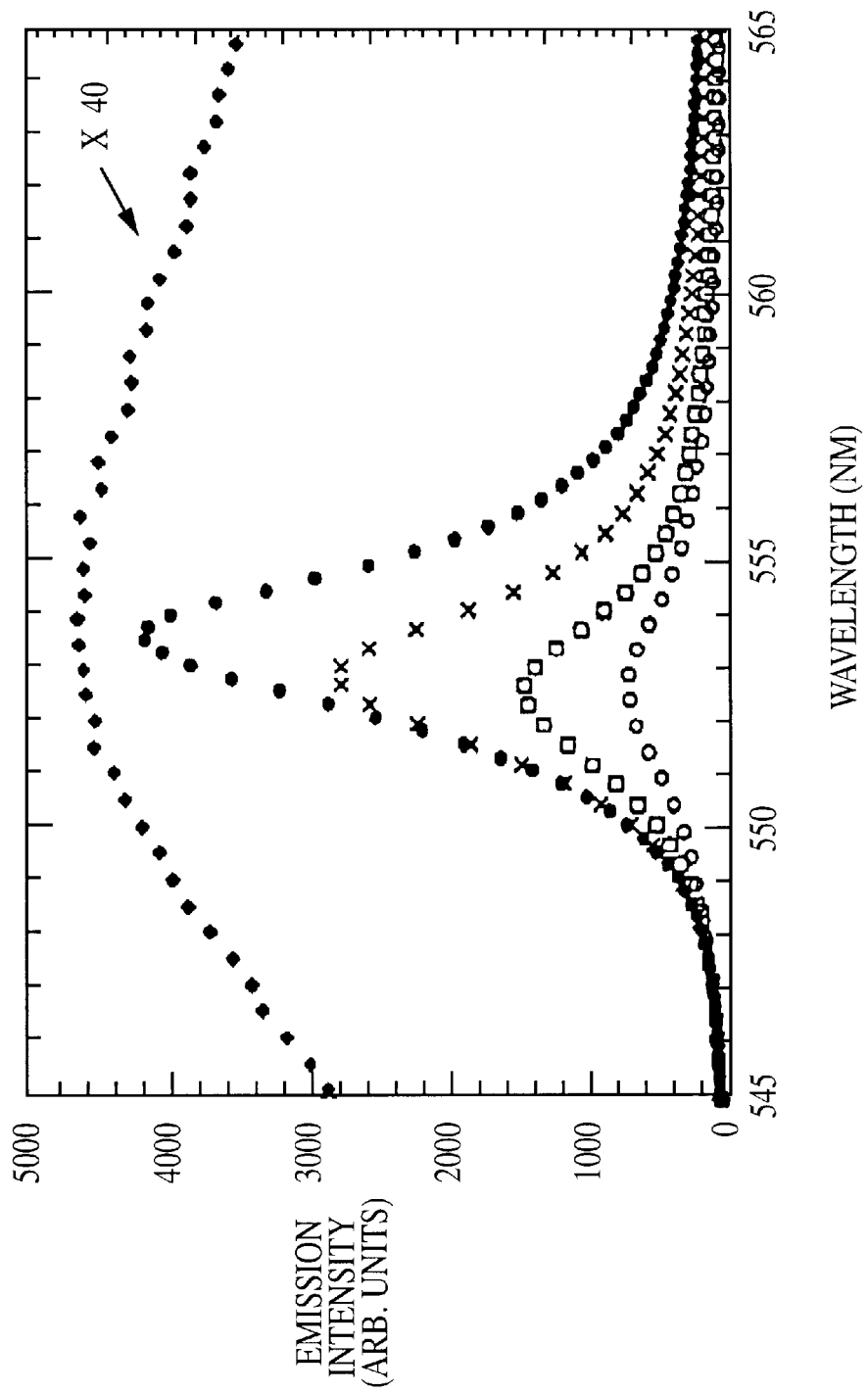

The spectra depicted in FIG. 9 show the variation in the optical emission from a laser dye solution, upon the introduction of random multiple scattering. In this series of spectral plots, the emission from a 1 milliliter (ml) methanol solution containing 1 mMolar Pyrromethene 567 (Lamda Physik, Inc) and a variable $TiO_2$ particle concentration was excited with the pulsed 532 nm laser source. The pulse energy of the excitation source was previously determined to exceed the stimulated emission threshold if the particle density in the media was in excess of $10^9/cm^3$. The particle-free dye solution exhibited weak and broad emission, which is typical behavior for spontaneous emission. Upon the addition of $2.3 \times 10^{10}/cm^3$ $TiO_2$ scatterers, however, a dramatic narrowing and enhancement was observed in the emission intensity.

As mentioned above, the multiple scattering increases the path length of the emitted photon in the high gain regions, which increases the level of amplification by stimulated emission. With the addition of more scatterers (scattering particles), the path length and amplification increase, narrowing the emission peak width (full width at half maximum) to a limiting value of ~3.6 nm at a particle density of $18.4 \times 10^{11}/cm^3$. At this level, the peak emission intensity is (as shown in FIG. 9) a factor of ~40 larger than the corresponding spontaneous emission from the neat dye solution. The results in FIG. 9 clearly illustrate the benefits of the stimulated emission in amplifying random media: intense, narrow spectral emission relative to the spontaneous emission profile.

Figure 10:
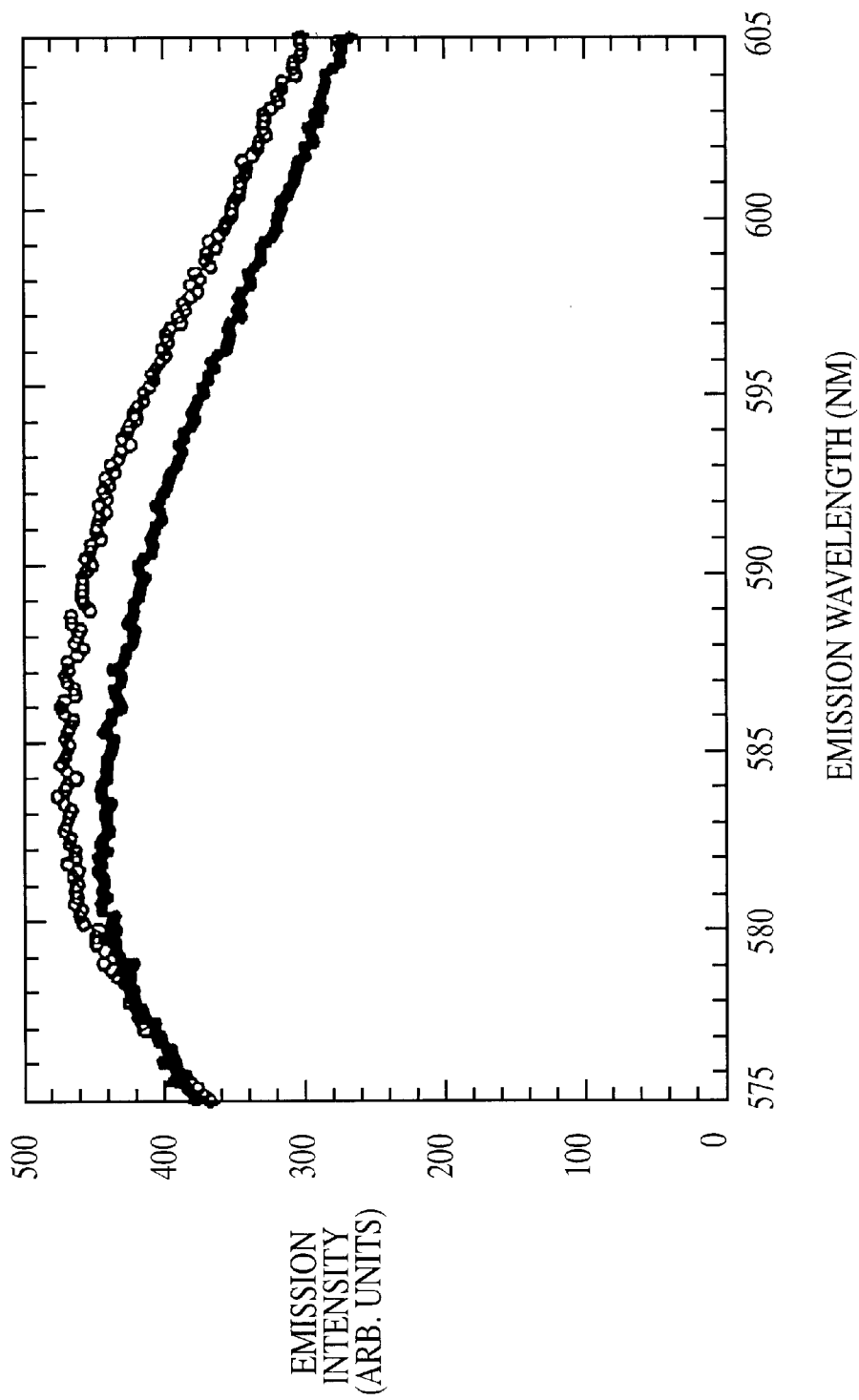
Figure 11:
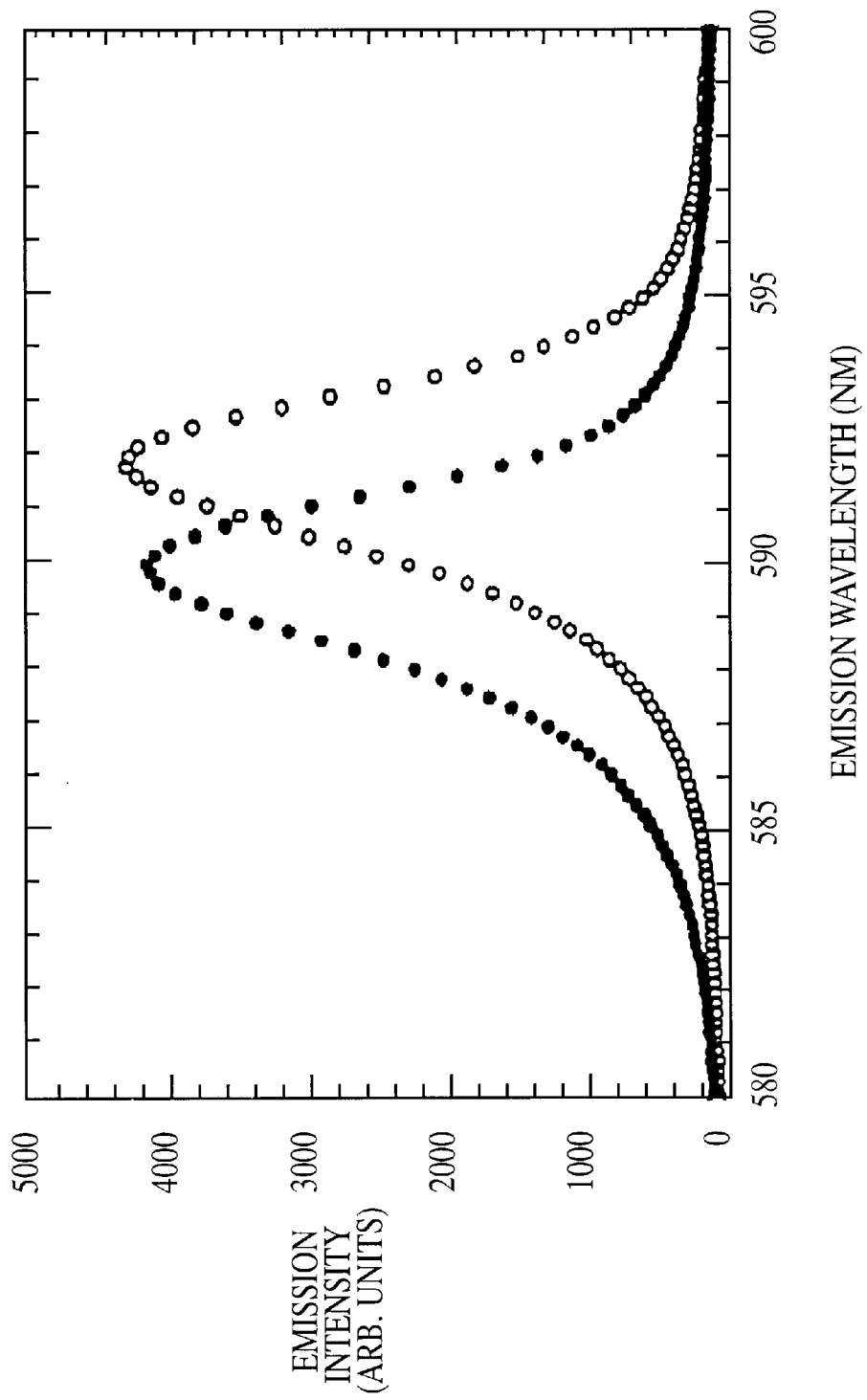

In addition to these studies, a series of measurements were made to examine the potential in using amplifying random media for chemical sensing applications. These optical investigations were designed to probe the effects of (1) solution basicity, and (2) the addition of an aromatic amine on the stimulated emission characteristics from the random media. In the basicity studies, the emission from a 0.5 ml methanol solution containing 1 mMolar Rhodamine 610 and a $TiO_2$ particle concentration of $4.6 \times 10^{10}/cm^3$ was probed before and after the addition of 1.2 liter of KOH. The spontaneous and stimulated emission results from the two solutions are shown in FIGS. 10 and 11 respectively.

In the spontaneous emission studies, excited with the 514.5 nm laser, there is a slight blue shift in the emission profile, and very little change in the peak intensity. The blue shift was previously observed in acid-base studies of Rhodamine dyes, and is attributed to the dissociation of the carboxyl group in the carboxyphenyl substituent of the Rhodamine 610 molecule (see FIG. 8).

In the stimulated emission results, the shift in the peak position (~2.5 nm) was comparable to the observed blue shift in the spontaneous emission. However, the narrow bandwidth of the stimulated response provides a much higher resolving power and ability to distinguish peak shifts of the dye emission. The enhanced sensitivity of the stimulated emission to peak position changes provides this response with a higher sensitivity to basicity modifications in the host media.

The influence of aromatic amines on the spontaneous and stimulated emission in amplifying random media was examined. In this investigation, the ability to detect small additions of benzylamine to a methanol solution composed of Carbazine 720 and $TiO_2$ scatterers, was probed by the stimulated emission from the solution mixture. The molecular structure of the carbazine dye (see FIG. 8) suggests that the aromatic amine will interact with the carbonyl functionality of the dye molecule when the analyte is introduced into the solution. The carbonyl functionality is part of the chromophore unit of the dye molecule, so the interaction between the carbonyl and the chromophore will influence the delocalized π-electron distribution in the chromophore and vary the absorption/emission profiles of the dye. As in the previous examination of the influence of the hydroxy radical (OH) on Rhodamine 610, the benzylamine interaction with the carbonyl groups decreased the non-radiative processes in the dye, and hence produced higher emission efficiencies. Therefore, the presence of benzylamine in the solution should be indicated by an increase in the Carbazine 720 emission.

The chemical structure of the DCM molecule indicates that an interaction with benzylamine is not likely to perturb the absorption or emission characteristics of this dye molecule. This was experimentally verified by examining the stimulated emission from a DCM random media solution both before and after the addition of benzylamine. The emission profiles from the two solutions (not shown) were indistinguishable, which assured that a variation in the stimulated emission from a DCM/Carbazine 720 binary dye solution could be attributed to the benzylamine/carbazine interaction.

Figure 12:
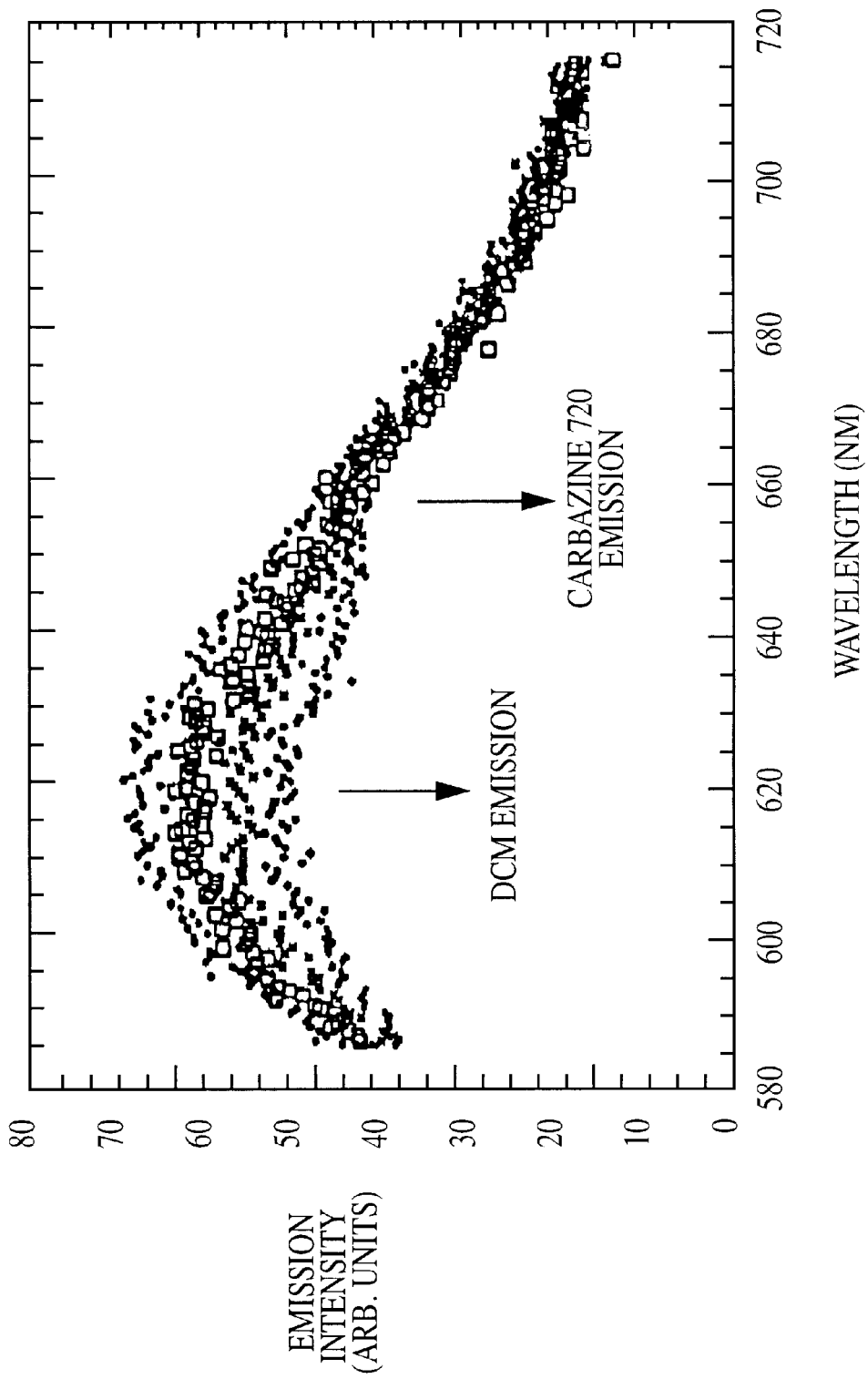
Figure 13:
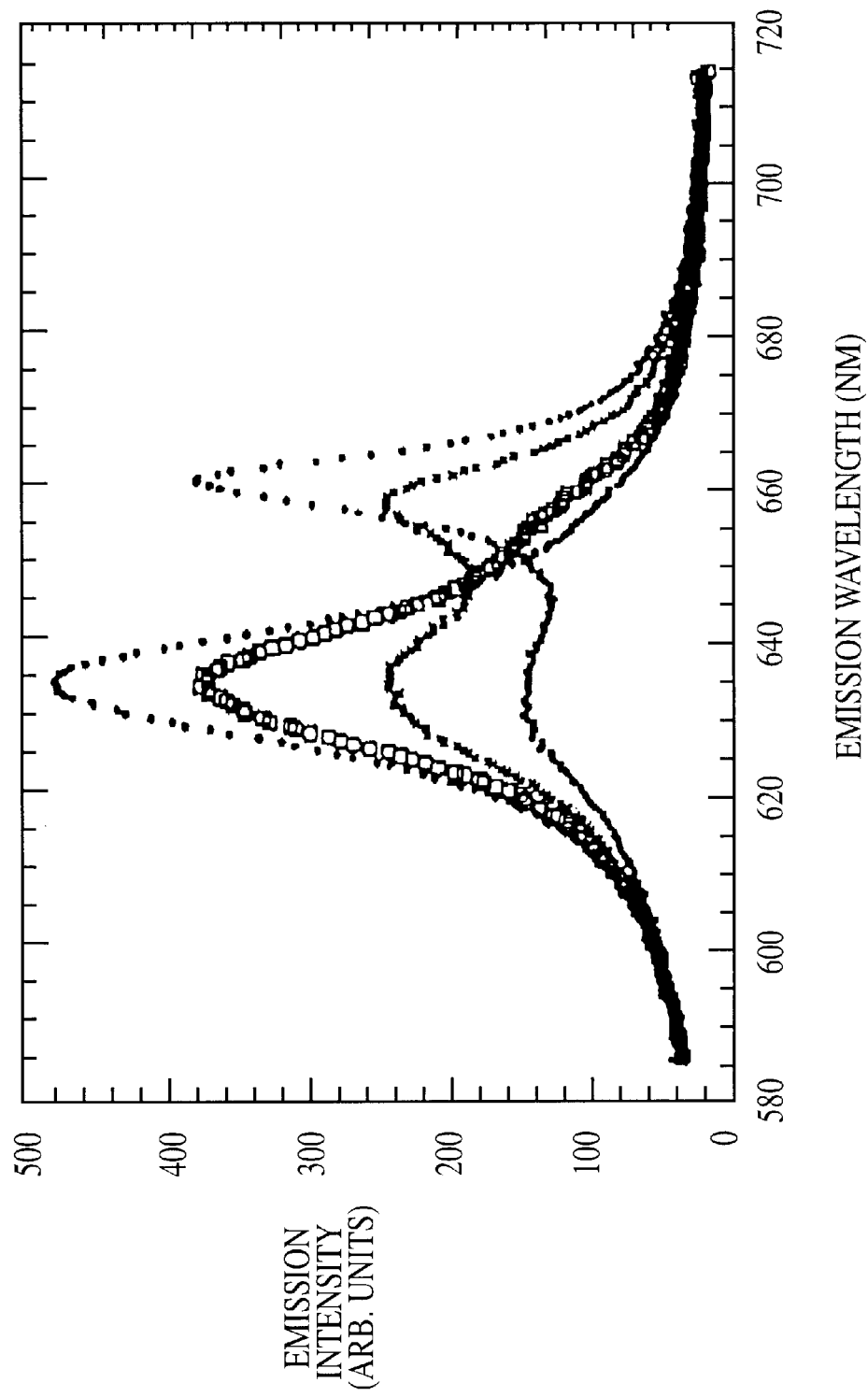

The results in FIGS. 12 and 13 show the effects of benzylamine addition on the spontaneous and stimulated emission profiles, respectively. In these studies, the dye concentrations in a 0.1 mliter solution of methanol were 1 mMolar DCM and 0.3 mMolar Carbazine 720, with a scatterer concentration of $1.2 \times 10^{11}/cm^3$. In the spontaneous emission results (514.5 nm input), the DCM component of the dye mixture generated a broad emission band at 620 run in the amine-free solution, with little or no emission from the carbazine component. The intensity of the DCM emission began to decrease with the addition of benzylamine, reaching a 25% reduction level when a total of 4 parts per million of the amine (relative to the Carbazine 720 concentration) was introduced into the solution.

The decrease in the DCM emission intensity upon the benzylamine addition was attributed to an increase in energy transfer between the DCM and Carbazine 720 molecules, which produced the appearance of a new broad emission peak at 660 nm. These results indicate that spontaneous emission from the binary dye solution has the ability to detect sub-nanogram levels of the aromatic amine in the random media. However, as in the previous basicity study, the chemical sensitivity tends to be attenuated, since it arises from an intensity variation rather than a wavelength shift in the emission profile.

In the stimulated emission results (pulsed 532 nm source), the spectra show sharp emission features that are attributed to the two dye components in the solution. In comparison to the spontaneous emission spectra, these features are markedly narrow and intense. In the amine-free solution, the DCM component of the binary dye mixture generated an emission band at 633 nm with a bandwidth of ~13 nm. Similar to the spontaneous emission from this solution composition, no Carbazine 720 emission feature was observed. A 200 parts per billion addition of benzylamine (relative to the Carbazine 720 concentration) reduced the DCM emission intensity by ~20% and introduced a shoulder at 660 mn, which is due to the onset of Carbazine 720 emission. As the benzylamine content of the solution was increased from 200 parts per billion to 4 parts per million, the DCM peak emission intensity decreased to a level that was ~20% the value in the amine-free spectrum. The Carbazine 720 peak emission became more pronounced with the continued additions of benzylamine, and narrowed to a bandwidth of ~8 mn. A comparison between the spontaneous and stimulated emission profiles from the high gain media shows that the intense, well-resolved emission features in the stimulated emission provides a significant enhancement for the chemical detection of the benzylamine addition. Although the spontaneous emission is able to sense the presence of the benzylamine, the weak and broad emission features limit the ability to detect the sub-nanogram additions in the random media solution. The intense, narrow emission features of the stimulated emission are much more amenable to the detection of the low concentration benzylamine additions.

The ability to sense other chemical analytes, such as carbon dioxide or other organic compounds, is limited only by the ability to select an energy transfer dye molecule pair (emitters A and B), which exhibits a chemical sensitivity to the analyte. In the above example, chemical mediation is demonstrated in a solvent system where emitter B was modified by the presence of benzylamine, which initiated efficient energy transfer from emitter A (DCM) to emitter B (carbazine 720). In a similar mediating manner, other chemical analytes such as simple acids and bases (pH), nucleic acids, carbon dioxide, metal ions (zinc and calcium), aromatic amines, cyanides, and thiols can initiate energy transfer between two carefully selected emitting-dyes. Listed below in Table 1, are examples of energy transfer dye pairs that exhibit efficient energy transfer in the presence of the respective chemical mediator. In all cases, emitter A is excited by the primary light source, and then transfers energy to emitter B.

TABLE 1

| Mediator | Emitter A | Emitter B |
|---|---|---|
| pH | Rhodamine green | seminaphthorhodfluor dyes* |
| nucleic acid | DCM | dimers of cyanine dyes* |
| carbon dioxide | coumarin dyes | hydroxypyrene trisulfonic acid* |
| metal ion | fluorescein | magnesium orange* |
| aromatic amine | anthracene dicarboxaldehyde* | BODIPY** |
| cyanide | naphthalene dicarboxaldehyde* | fluorescein |
| thiol | CBQCA* | BODIPY** |

*Chemically modified emitter

Information about these dye emitters was obtained from 'Handbook of Fluorescent Probes and Research Chemicals," Richard P. Haugland, editor, Product Catalog for Molecular Probes, Inc. The double asterisk represents a trademark name.

In addition to other chemical mediators, the composition of the scatterer can also be varied. In the present example, sub-micron sized titania was used as the inert (optically inactive) scatterer in the media. The constraints on other scatterer material are (1) high dielectric constant (larger than the media background), and (2) low optical absorption coefficient at the excitation and emission wavelengths. Examples of particulate materials that have been examined are (1) silicon carbide, (2) diamond, (3) alumina, (4) barium titanate, and (5) zinc oxide.

It will be appreciated that although the present invention has been disclosed with reference to only a limited number of examples, the concept upon which the invention is based can be applied in various ways. The narrow emission and high intensity characteristics of random, high optical gain systems are well-suited for photonic identification applications that are utilize the concept of "spectral bar codes". For example, it has already been demonstrated that spectral emission "codes" can be created in random, high gain media lasers when an appropriate selection of dye molecules and scatterers are embedded In a polymer host.

Another class of potential applications afforded random, high gain media is their incorporation into chemical and biological sensor systems. In part, this direction is based on optical sensor systems that utilize spontaneous emission from indicator molecules for the detection of low molecular weight organics and complex biological agents. The emission from random, high gain media is a logical extension of the current optical sensor technology, since the stimulated emission process is sensitive to variations in both the emission properties of the dye molecule and the gain profile of the random media.

Figure 14:
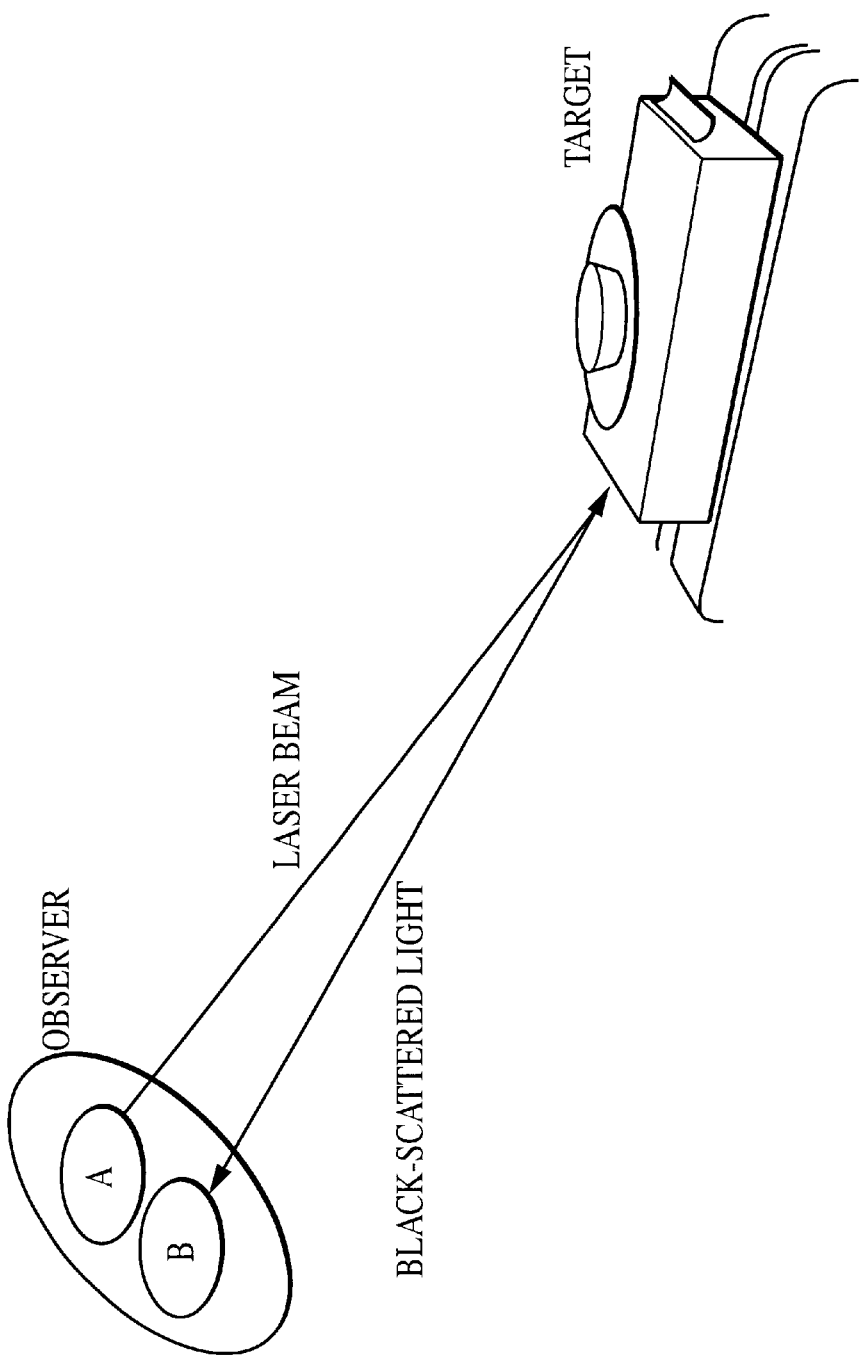
FIG. 14 is a schematic sketch showing an example of how a taggant, utilizing the concept of the present invention, can be used to identify an object at a remote location.

FIG. 14 shows the application of a taggant according to the invention used on a vehicle. In this arrangement, a laser A (having sufficient pulse energy to generate stimulated emission) is used to irradiate the surface of the tank while suitable optical equipment B is used to observe the back-scattered light and to determine if this light contains the appropriate narrow frequency band emission or exhibits a shift in accordance with some controllable aspect of the taggant.

More specifically, with taggants it is possible to introduce a further element which will inhibit the effect of a mediating analyte or block photonic emissions until such time as predetermined conditions are met. Merely by way of example, it is possible that an agent, which is responsive to a predetermined stimulus, will not undergo a change in either chemical or physical properties until the stimulus is received. During this time, the agent will prevent either the shift, will produce an emission distinct from that expected from the first and second emitters, or the like. However, upon being induced to undergo a change, which removes the blocking/inhibiting function, the expected characteristics of the emitter mixture will be rendered observable.

This, of course, opens the door to a two beam type of arrangement, a time delayed action, an electromagnetic field influence, a temperature response and so on. If a "window" of some description, can be selectively controlled either chemically or physically, an additional stage/control feature becomes possible. In the case of a physical window, a liquid crystal window can be used to black out the taggant until some form of control renders it transparent.

For further reference with respect to the background of the invention and/or the chemicals/reagents/materials and the like, which can be considered for use in connection with the invention as disclosed supra, reference can be had to U.S. Pat. No. 5,763,891 issued to Yoshinaga, et al. on Jun. 9, 1998; U.S. Pat. No. 5,498,549 issued to Nagel et al. on Mar. 12, 1996; U.S. Pat. No. 5,943,354 issued on Aug. 24, 1999, in the name of Lawandy; U.S. Pat. No. 5,448,582 issued on Sep. 5, 1995 in the name of Lawandy; U.S. Pat. No. 5,811,152, issued on Sep. 22, 1998 in the name of Cleary; U.S. Pat. No. 5,434,878 issued on Jul. 18, 1995 in the name of Lawandy; U.S. Pat. No. 5,326,692 issued on Jul. 5, 1994 in the name of Brinkley et al; U.S. Pat. No. 5,643,728, issued on Jul. 1, 1997 in the name of Slater et al.; and U.S. Pat. No. 4,131,064 issued on Dec. 26, 1978 in the name of Ryan et al. The disclosure of each of this reference is hereby incorporated by reference thereto.

It is submitted that the scope of the invention is limited only by the appended claims and is not influenced by the number of examples discussed which are, given the concept of the invention, more than ample to permit a person skilled in this art to develop various modifications/adaptations without the need for inventive activity.

What is claimed is:

1. A photonically excitable arrangement comprising:
   a first material which is capable of absorbing and emitting photonic energy and which, when sufficiently excited by photonic energy from an external source, emits stimulated radiation in a first narrow wavelength band;
   a second material which is capable of absorbing and emitting photonic energy; and
   a mediating material which causes the photonic emission of the first material to be transferred to the second material which is excited to emit stimulated radiation in a second narrow wavelength at least partially in place of the emission from the first material in the first narrow wavelength band.

2. An arrangement as set for in claim 1, further comprising a host material in which the first and second materials are dispersed.

3. An arrangement as set forth in claim 1, further comprising scattering particles dispersed amongst the first and second materials for scattering emissions from the first material to the second material.

4. An arrangement as set forth in claim 1, wherein the mediating material is selected to modify the first material and to change at least one of its characteristics to a degree that the photonic radiation which is emitted from the first material under stimulated conditions, is changed to a form wherein it is absorbed by the second material.

5. An arrangement as set forth in claim 1, wherein the external source comprises a laser.

6. An arrangement as set forth in claim 5, wherein the laser is a pulsed laser

7. An arrangement as set forth in claim 6, wherein the laser is a YAG laser.

8. An arrangement as set forth in claim 7, wherein the YAG laser is a doubled Nd:YAG laser emitting a 532 nm, 7 nanosecond pulse.

9. An arrangement as set forth in claim 5, wherein the laser is a continuous wave laser.

10. An arrangement as set forth in claim 9, wherein the continuous laser is an argon ion laser with a 514.5 nm wavelength.

11. An arrangement as set forth in claim 3, wherein the scattering particles are particles selected from the group consisting essentially of: silicon carbide, diamond, alumina, barium titanate, zinc oxide and titanium dioxide.

12. An arrangement as set forth in claim 1, wherein the first material is a dye.

13. An arrangement as set forth in claim 1, wherein the first material is selected from the group consisting essentially of: rhodamine green, DCM, coumarin dyes, fluorescein, anthracene dicarboxaldahyde, napththalene dicarboxaldahyde.

14. An arrangement as set forth in claim 1, wherein the second material is a dye.

15. An arrangement as set forth in claim 1, wherein the second material is selected from the group consisting essentially of: seminaphthorhodfluor dyes, dimers of cyanine dyes, hydroxypyrene trisulfonic acid, magnesium orange, BODIPY, fluorescein, and carbazine.

16. An arrangement as set forth in claim 2, wherein the host material is one of a liquid and a solid.

17. An arrangement set forth in claim 2, wherein the host is a polymer, gel, or glass structure formed to have a predetermined permeability to fluid material.

18. An arrangement as set forth in claim 1, wherein the mediating material is selected from the group consisting essentially of: nucleic acid, carbon dioxide, a metal ion, aromatic amine, cyanide, and thiol.

* * * * *